(12) United States Patent
Cobianu et al.

(10) Patent No.: US 9,557,289 B2
(45) Date of Patent: Jan. 31, 2017

(54) LEAD-FREE ELECTROCHEMICAL GALVANIC OXYGEN SENSOR

(75) Inventors: Cornel Cobianu, Bucharest (RO); Bogdan-Catalin Serban, Bucharest (RO); Bryan Stewart Hobbs, West Sussex (GB)

(73) Assignee: Life Safety Distribution AG, Hegnau (CH)

(*) Notice: Subject to any disclaimer, the term of this patent is extended or adjusted under 35 U.S.C. 154(b) by 350 days.

(21) Appl. No.: 14/241,271

(22) PCT Filed: Sep. 14, 2011

(86) PCT No.: PCT/RO2011/000022
§ 371 (c)(1),
(2), (4) Date: Feb. 26, 2014

(87) PCT Pub. No.: WO2013/039414
PCT Pub. Date: Mar. 21, 2013

(65) Prior Publication Data
US 2014/0231253 A1   Aug. 21, 2014

(51) Int. Cl.
*G01N 27/413* (2006.01)
*G01N 27/404* (2006.01)

(52) U.S. Cl.
CPC .......... *G01N 27/413* (2013.01); *G01N 27/404* (2013.01)

(58) Field of Classification Search
CPC ..................................... G01N 27/404–27/4045
USPC ......................................... 204/431–432, 415
See application file for complete search history.

(56) References Cited

U.S. PATENT DOCUMENTS

| 3,223,597 A | | 12/1965 | Hersch | |
| 3,616,416 A | * | 10/1971 | Linenberg | H01M 12/06 204/400 |
| 4,539,086 A | * | 9/1985 | Fujita | C25B 1/02 204/263 |
| 4,652,359 A | * | 3/1987 | Niedrach | G01N 27/404 204/402 |
| 4,894,138 A | * | 1/1990 | Gambert | G01N 27/404 204/415 |
| 5,200,044 A | | 4/1993 | Milstein et al. | |

(Continued)

FOREIGN PATENT DOCUMENTS

CN    2241341 Y    11/1996
CN    2254552 Y    5/1997

(Continued)

OTHER PUBLICATIONS

China Office Action and Search Report, dated Jan. 15, 2016, corresponding to China Patent Application No. 201180074816, 9 pages.

(Continued)

*Primary Examiner* — Bach Dinh
(74) *Attorney, Agent, or Firm* — Conley Rose, P.C.; Kristin Jordan Harkins

(57) ABSTRACT

A lead-free, self-corrosion-free electrochemical galvanic oxygen sensor is provided. The preferred sensor includes a container, the container including a lead-free anode, an alkali electrolyte, a carbon platinized with platinum cathode and a nickel wire current collector, wherein the container further includes a diffusion barrier that causes the sensor to operate in the limiting current region.

9 Claims, 7 Drawing Sheets

(56) References Cited

U.S. PATENT DOCUMENTS

| | | | | |
|---|---|---|---|---|
| 5,650,054 A | * | 7/1997 | Shen | ............ G01N 27/4045 204/412 |
| 2002/0166776 A1 | * | 11/2002 | Fikus | ............ G01N 27/404 205/782 |
| 2007/0272553 A1 | | 11/2007 | Gambert | |
| 2010/0170795 A1 | * | 7/2010 | Cowburn | ............ G01N 27/404 204/406 |

FOREIGN PATENT DOCUMENTS

| | | |
|---|---|---|
| DE | 10 2006 024 022 A1 | 11/2007 |
| EP | 0 180 161 A2 | 5/1986 |
| EP | 0180161 A2 | 5/1986 |
| EP | 1 593 962 A1 | 11/2005 |
| EP | 2 219 024 A1 | 8/2010 |

OTHER PUBLICATIONS

China Office Action and Search Report, dated Jul. 20, 2015, corresponding to China Patent Application No. 201180074816, 11 pages.
English translation of abstract of DE102006024022 (A1).
International Search Report, dated Jun. 19, 2012, corresponding to International Application No. PCT/RO2011/000022.

* cited by examiner

POTENTIAL-pH EQUILIBRIUM DIAGRAM FOR THE SYSTEM LEAD-WATER, AT 25°C

POTENTIAL-pH EQUILIBRIUM DIAGRAM FOR THE SYSTEM ANTIMONY-WATER, AT 25°C

POTENTIAL-pH EQUILIBRIUM DIAGRAM FOR THE SYSTEM BISMUTH-WATER, AT 25°C

POTENTIAL-pH EQUILIBRIUM DIAGRAM FOR THE SYSTEM ANTIMONY-WATER, AT 25°C

POTENTIAL-pH EQUILIBRIUM DIAGRAM FOR THE SYSTEM BISMUTH-WATER, AT 25°C

POTENTIAL-pH EQUILIBRIUM DIAGRAM FOR THE SYSTEM COOPER-WATER, AT 25°C
[CONSIDERING THE SOLID SUBSTANCES CU, $CU_2O$ AND CuO, $CU[OH]_2$ IS NOT CONSIDERED]

LEAD-FREE ELECTROCHEMICAL GALVANIC OXYGEN SENSOR

FIELD

The field relates to oxygen sensors and more particularly to galvanic oxygen sensors.

BACKGROUND

Galvanic oxygen sensors are generally known. Such devices are typically constructed with a lead anode because of its reliability, stability and ease of manufacture.

However, lead is a known toxic material that should be eliminated from electronic packaging, chemical sensing and other commercial applications, due to its demonstrated deleterious effect on people's health. In recent years, there has been intensive research directed to developing lead-free oxygen galvanic sensors, as a drop-in replacement for existing portable gas detection instruments.

In general, low power/no power consumption oxygen sensors are the most attractive technical solution for portable applications because they offer the maximum operating time between re-charging periods. The major advantage of oxygen galvanic sensors for portable instruments is the fact that they are self-powered, and they have a simple signal conditioning circuit for sensor read-out, consisting of a load resistor connected between the consumable anode and the cathode and/or a current follower circuit.

Recently developments have proposed the use of different base metals like zinc, aluminum and tin (EP 1 593 962 A1, and EP 2 219 024 A1) as a possible replacement for the lead anode in electrochemical galvanic oxygen sensors with consumable anodes. However, it is difficult to control the rate of consumption of the anode using such metals working in a capillary limited mode.

In general, a projected lifetime of at least two years is necessary for possible substitutes for lead anodes in electrochemical galvanic oxygen sensors. However, it does not appear that such lifetimes can be achieved using metals such as zinc, aluminum or tin. Accordingly, a need exists for other alternatives in the construction of electrochemical galvanic oxygen sensors.

DETAILED DESCRIPTION OF AN ILLUSTRATED EMBODIMENT

Figure 1:
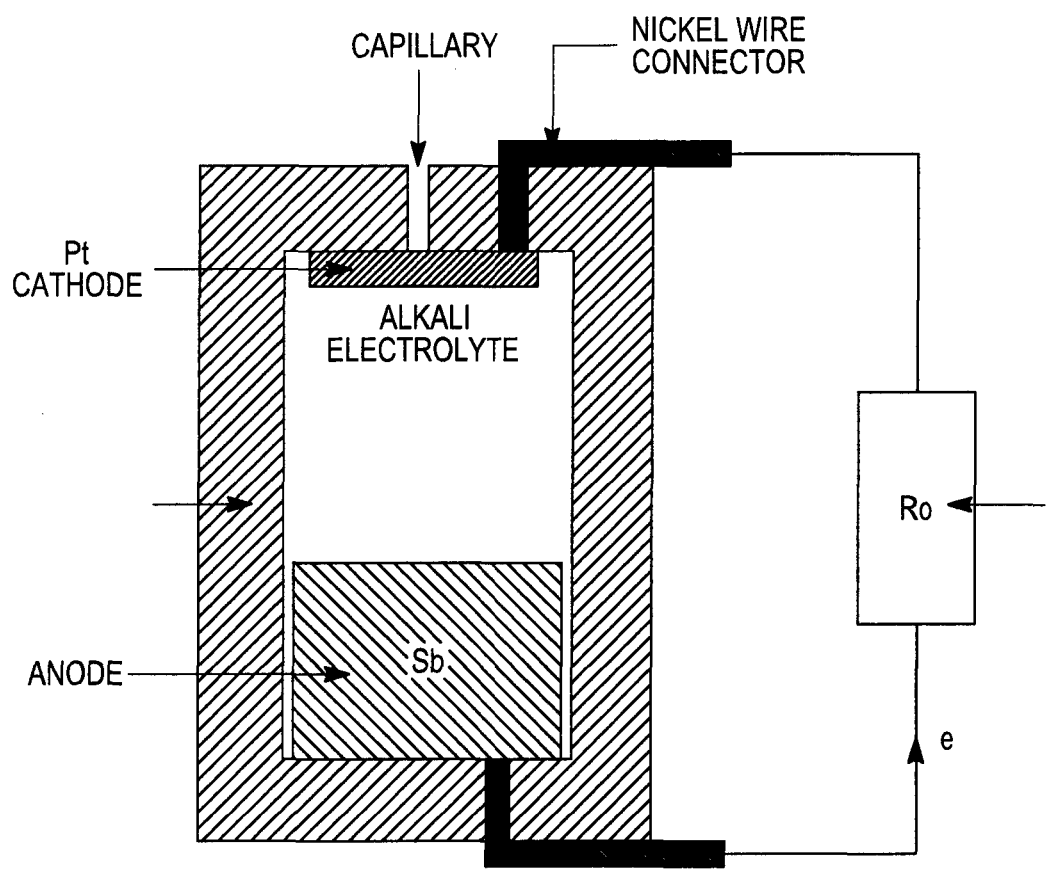
FIG. 1 depicts an electrochemical galvanic gas sensor in accordance with an illustrated embodiment.

FIG. 1 depicts an electrochemical galvanic oxygen sensor 10 shown generally in accordance with one illustrated embodiment. The sensor 10 may be constructed with a plastic or metal container or housing 12. Included within the housing 12 is a platinum cathode 14, an anode (e.g., antimony (Sb), bismuth (Bi) or copper (Cu)) 16 and an electrolyte 18. The cathode 14 and anode 16 may be coupled to an external load resistor (e.g., 100 ohms) 24 via a set of nickel wire collectors 22. Other cathode materials which may be used include, but are not restricted to, gold, silver or platinized carbon. In addition, while the current collector 22 of FIG. 1 shows a very specific structure, the current collector 22 contemplated herein includes any structure whereby electrical connection is made from an external circuit to the electrode(s) including, but not restricted to, a metal wire feeding from the exterior of the sensor housing to said electrode or an extension of the electrode itself to the exterior of the sensor housing.

The sensor 10 may be provided with a diffusion control device 20 associated with the sensor lid. The diffusion control device may be a capillary extending through the lid with a predetermined diameter and length (e.g., 50 micrometers in diameter by 2 mm in length) and/or a diffusion membrane of a predetermined permeability which limits air admission to the platinum sensing electrode 14, and/or a solid diffusion barrier in which oxygen is soluble and mobile.

Under these conditions and in the context of the $O_2$ galvanic sensor designs described below, it has been found that the sensor 10 will work in the diffusion-limited (DL) regime, i.e., the rate of $O_2$ molecule diffusion through the sensor capillary or membrane is much slower than the reaction velocity taking place at the cathode (reduction of $O_2$ molecules on the platinum electrode) or at the anode (oxidation of material, which is thus consumed, followed by electron generation and their trip to the cathode by the external circuit, where needed for $O_2$ reduction). Within this DL regime, an I-V characteristic is obtained for the $O_2$ sensor 10, where a constant current region is present (limiting current region), even if the cell voltage varies due to electrochemical changes in the electrolyte or because of partial passivation of the anode surface by means of reaction products. Such saturation current of the sensor is proportional to the $O_2$ concentration in the air. The cell voltage variation for which the sensor current remains unchanged is referred to herein as the voltage window (VW), and this should be a positive value with respect to a standard referred to as the normal hydrogen electrode (NHE) potential. Such window can be experimentally measured on the $O_2$ sensor 10.

Figure 3:
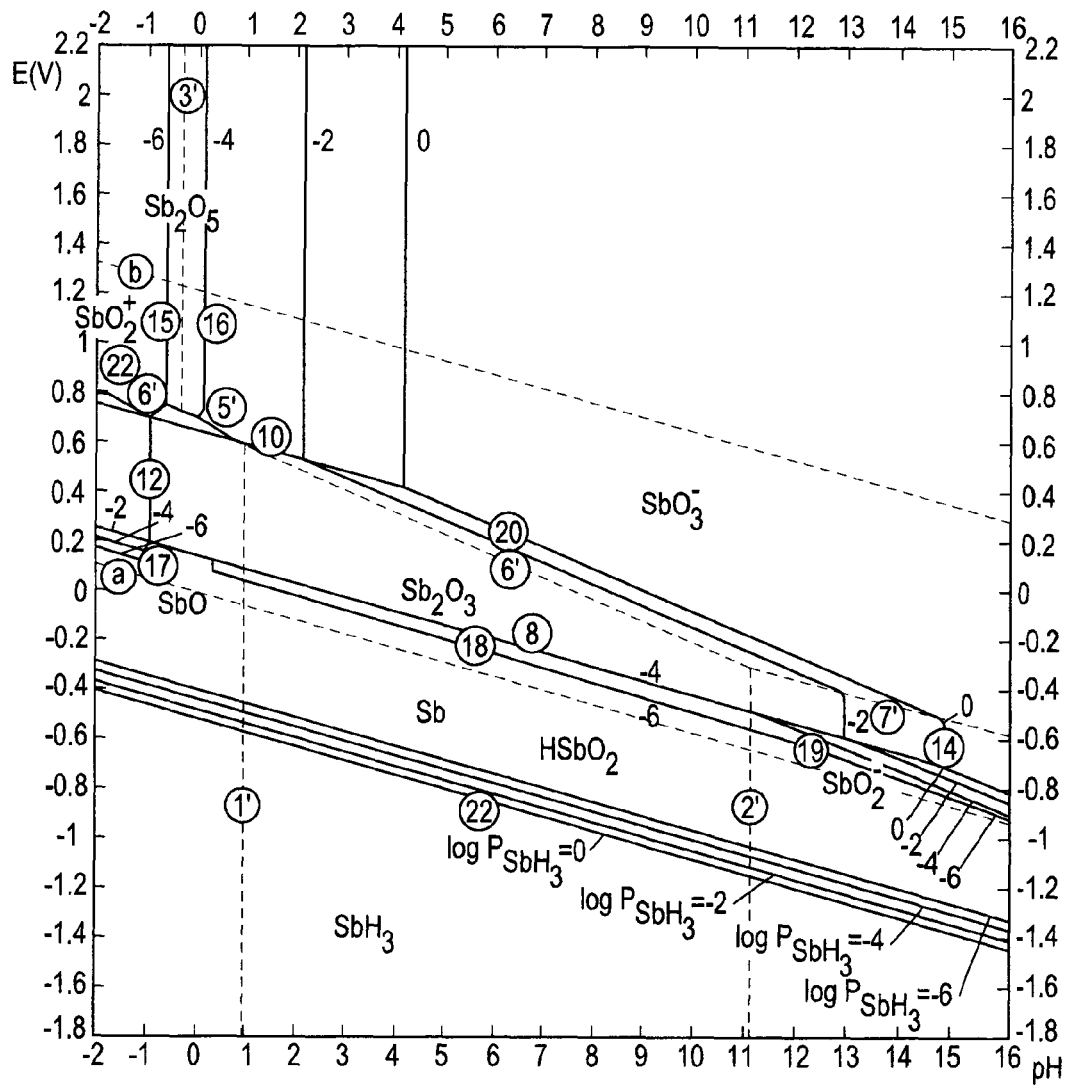
FIG. 3 is a Pourbaix diagram for antimony in aqueous solutions.
Figure 4:
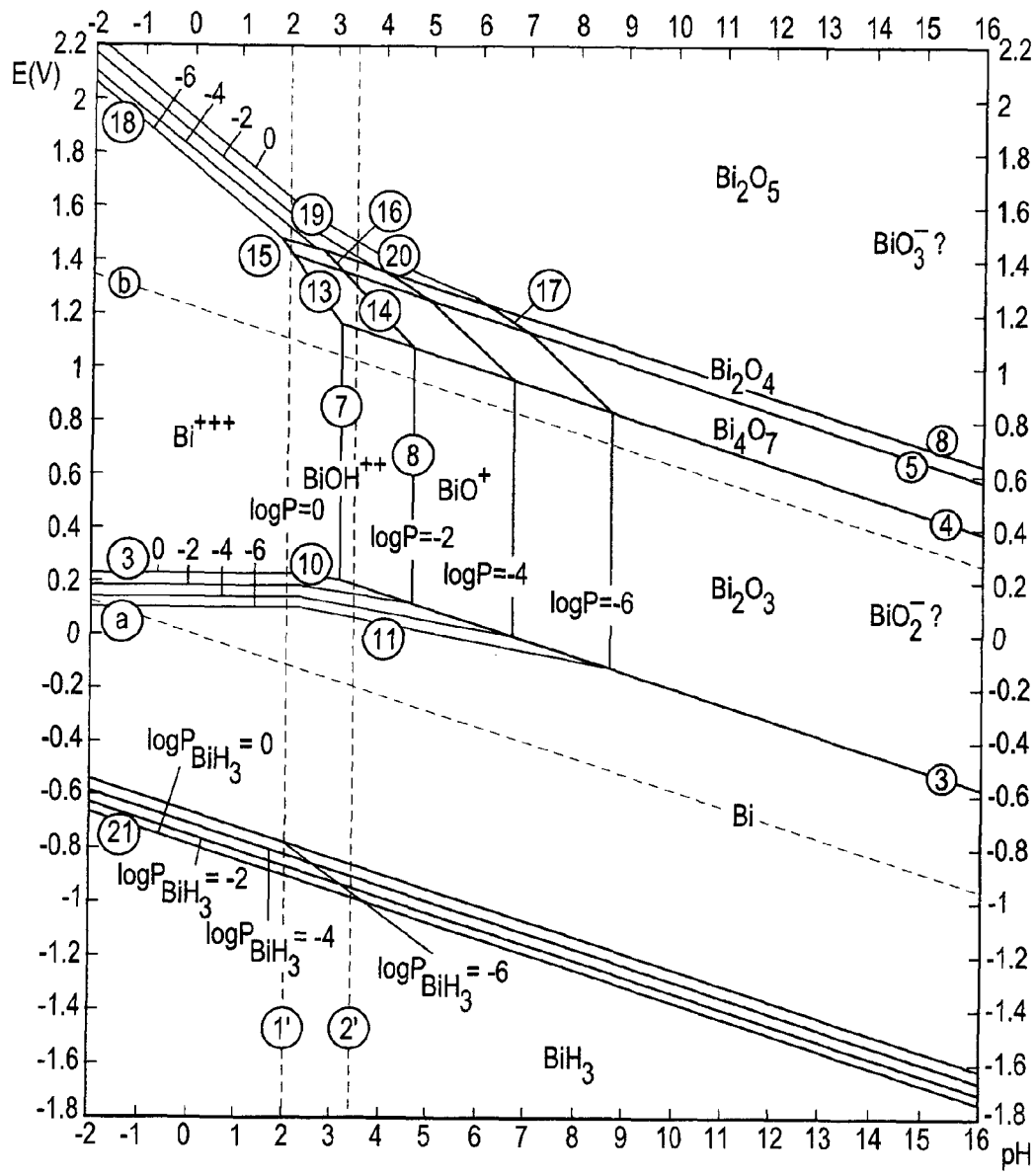
FIG. 4 is a Pourbaix diagram for bismuth in aqueous solutions.

On the other hand, it has been found that a theoretical estimation of the thermodynamic voltage window (TVW) can be made from analysis of the Potential-pH equilibrium diagram of each anode candidate in aqueous solution, by subtracting the potential of a Me/Metal oxide oxidation reaction (where Me is either Cu, or Sb, or Bi) from the $H_2O/O_2$ water oxidation reaction (line (b) in the Pourbaix diagram for the metal Me), in the same electrolyte. As discussed below and as shown in FIGS. 3 and 4, the TVW is highest for the case Sb (about 1.076 V), while for the case of Bi this TVW is equal to about 0.857 V. From this point of view, one can estimate that the VW, value of Sb is higher than the corresponding value for Bi (0.857 V) or lead (0.98V), where the EVW of lead is used as a reference sensor.

According to the theoretical results of equilibrium reactions between metals and aqueous solutions, another important attraction of Sb anodes is the possible solubility of the oxidation reaction products in alkali electrolytes, which minimises the risk of passivation of the free anode surface, if precautions were taken to avoid having other parasitic reactions at the anode. In addition, the good energy capacity of Sb and the relative low mass needed for a two year minimum lifetime of sensor operation further suggest that Sb may be a strong candidate for lead replacement. Due to the above electrochemical characteristics and the fact that Sb and Bi are not present on the list of prohibited materials used by many countries, these elements become strong candidates as replacements for lead.

If one looks at the well-known thermodynamic nobility scale, one can see that for elements ranked after lead (position 19 in the thermodynamic nobility scale), there is a very small thermodynamic immunity region and therefore, a user cannot select them as appropriate materials for a sensor anode, without the risk of self-corrosion, not to mention many country's demands to exclude cadmium and mercury from industrial applications. In the case of elements ranked in front of lead on the thermodynamic nobility scale (position 19), some of them are very toxic (e.g., Arsenic-position 17), or radioactive (e.g., Polonium-position 12, or Technetium-position 14), and are excluded from selection. In addition, going up from Pb toward more noble metals, the candidate materials cannot go beyond copper (position 13) due to the risk of getting a low TVW, which may indicate a rather low lifetime and/or poor performance at low temperatures due to low activity reserve.

Figure 2:
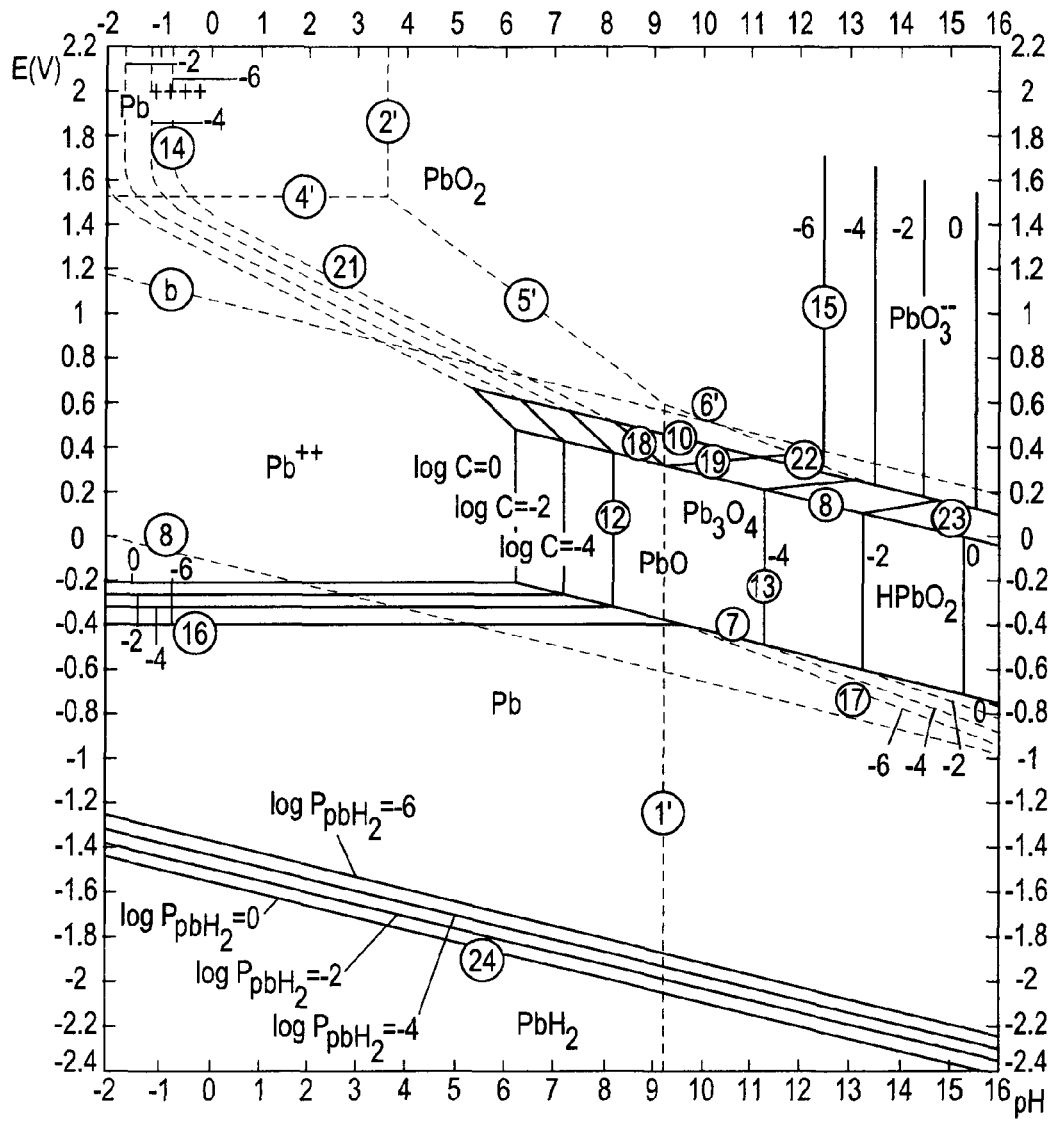
FIG. 2 is a Pourbaix diagram for lead.

In general, the good thermodynamic stability of lead, in the pH domain from 8 to 11, and its easy manufacturability has driven its extensive use in the past for anodes in $O_2$ galvanic sensors, and therefore lead can be used as a reference anode material (FIG. 2), when selecting replacements alternatives.

Figure 5:
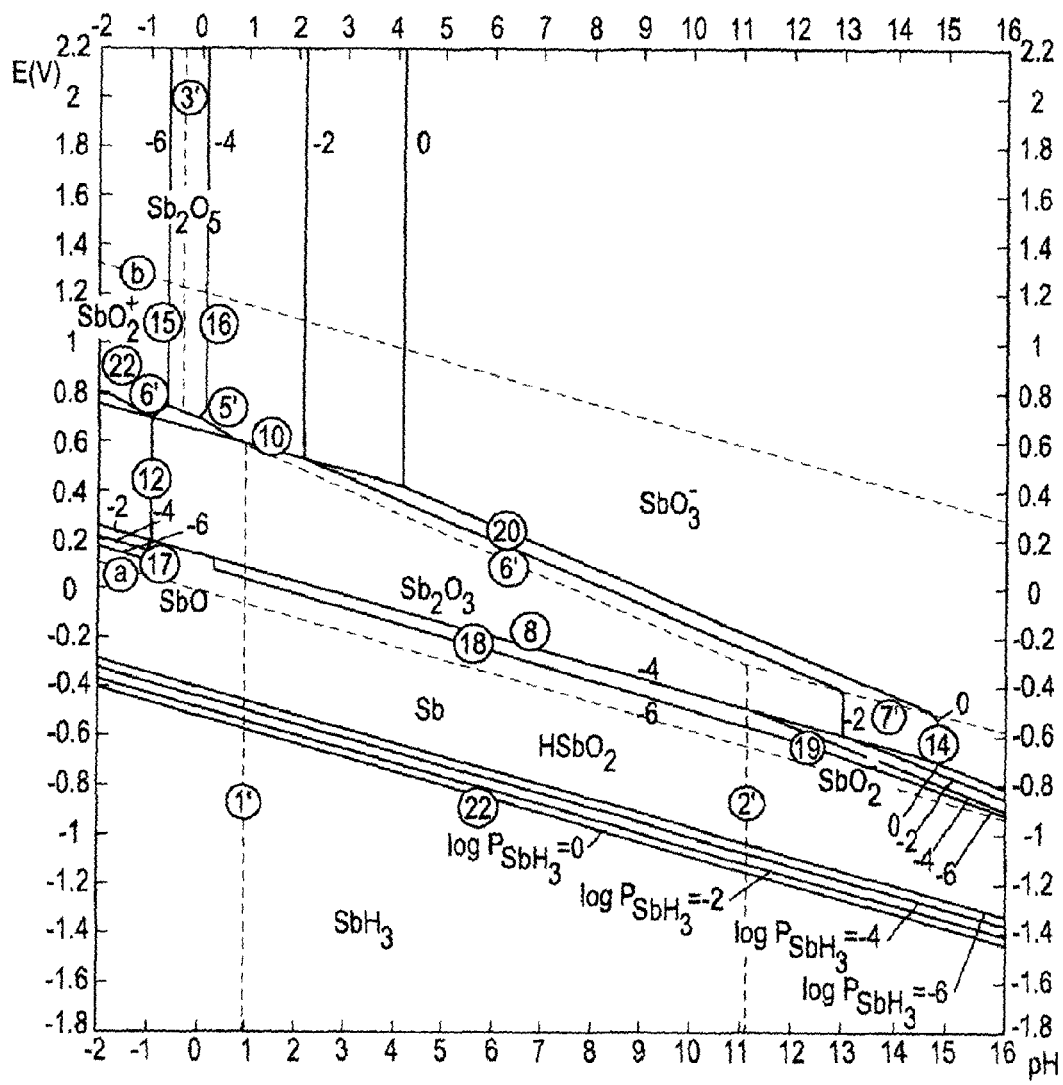
FIG. 5 is a calculation of the thermodynamic voltage window for antimony in alkali solutions from its Pourbaix.
Figure 6:
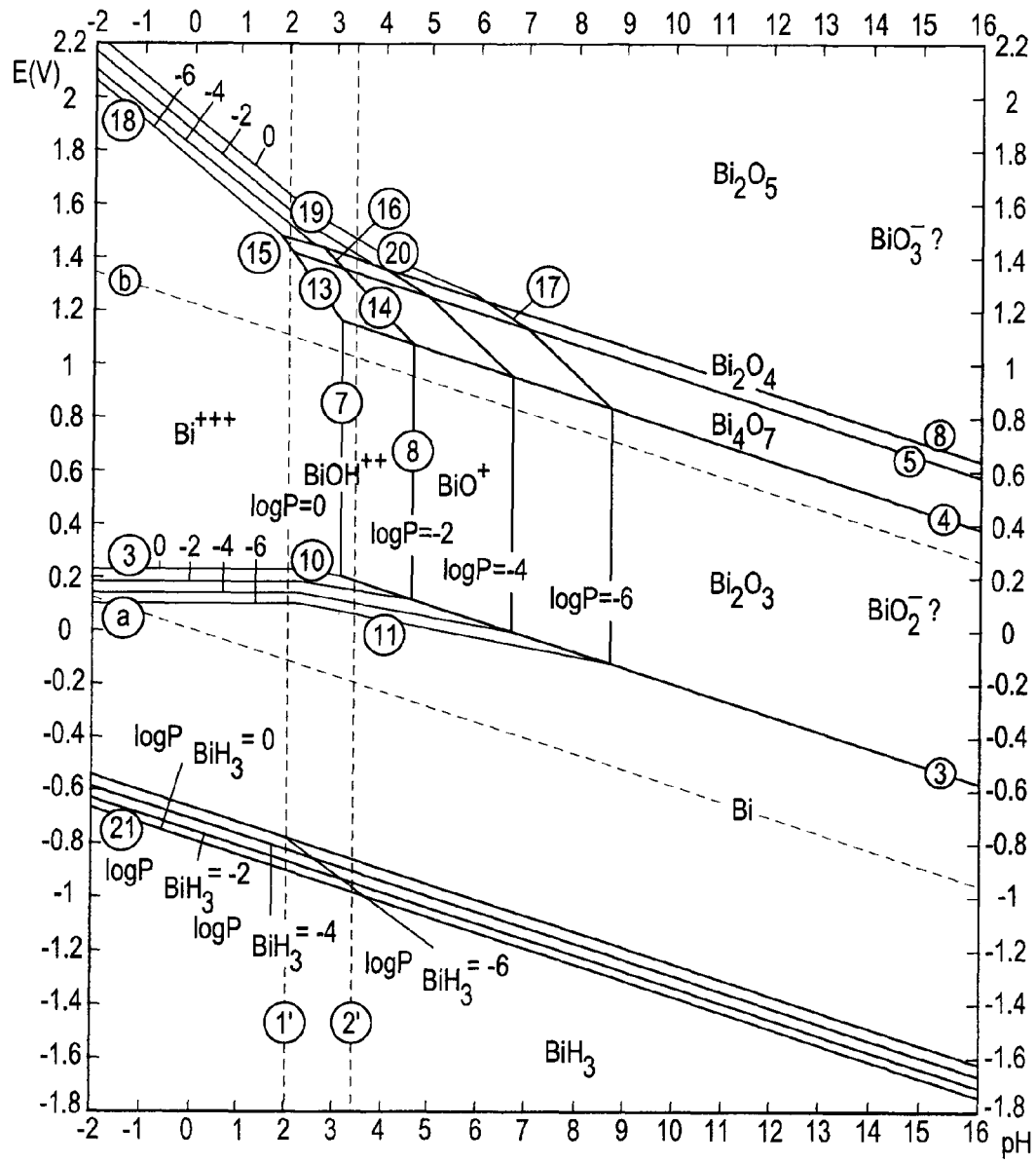
FIG. 6 is a calculation of the thermodynamic voltage window for bismuth in alkali aqueous solutions from its Pourbaix diagram.
Figure 7:
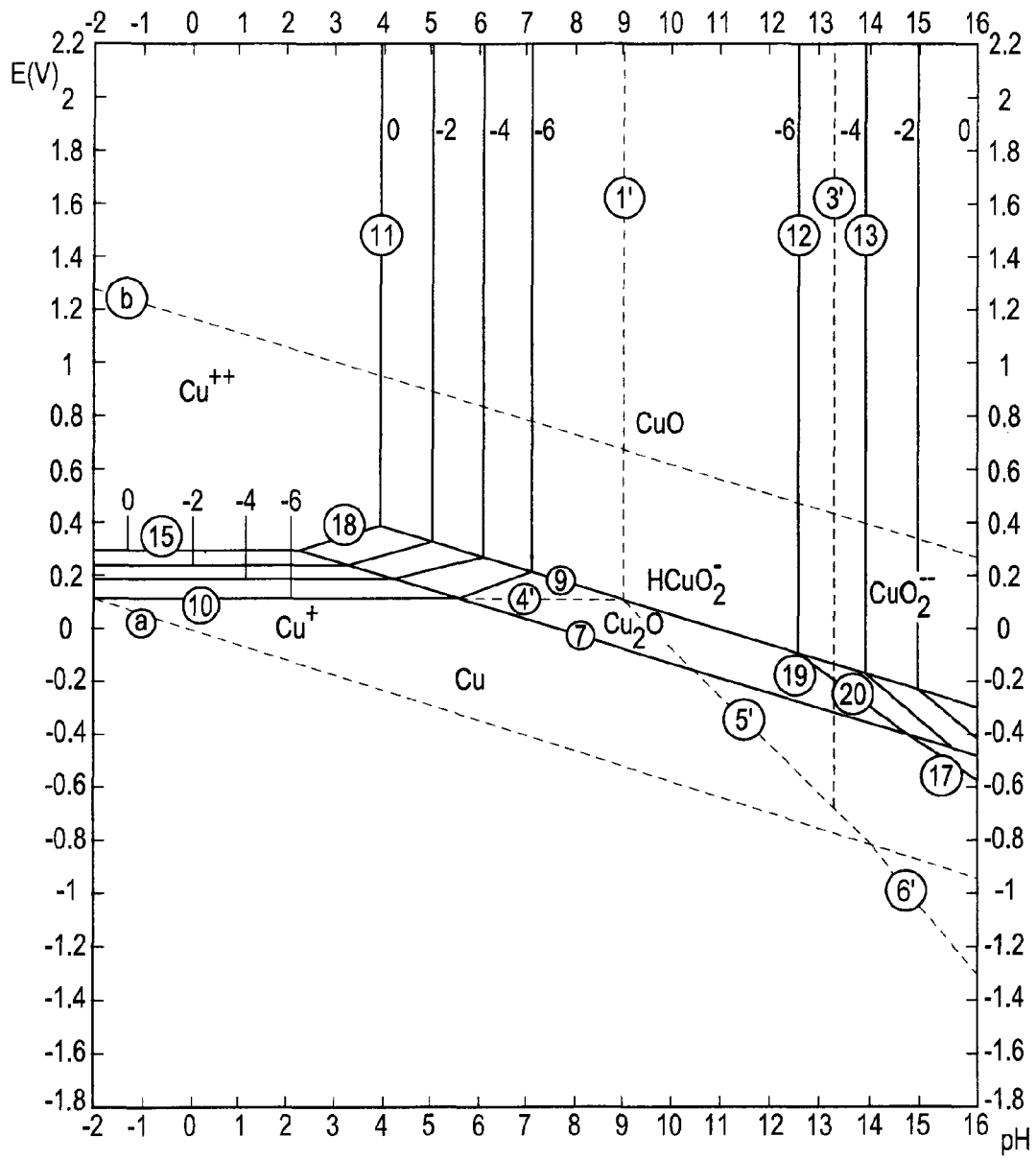
FIG. 7 is a Pourbaix diagram for copper in aqueous electrolytes.

FIGS. 3 and 4, shows the Potential-pH equilibrium diagrams of antimony and bismuth, respectively, and how the (theoretical) thermodynamic voltage windows may be calculated for these metals immersed in alkali aqueous solutions. FIGS. 5-7 are the Pourbaix equilibrium diagrams for Sb, Bi, Cu placed in aqueous solutions. (The Pourbaix equilibrium diagrams may be used to theoretically describe the novel $O_2$ galvanic sensing concepts for these anode materials immersed in acid or alkali electrolytes, at equilibrium conditions (no electric current flowing through the sensors).) The pH-V diagrams of FIGS. 5 and 6 show that the oxidation potentials of Sb or Bi ($Sb/Sb_2O_3$, or $Bi/Bi_2O_3$) are above the $H_2$ line, by about 0.15 V or 0.37 V, respectively, in an alkali electrolyte and therefore no self-corrosion is expected to occur. Thus, antimony or bismuth can be used to make an $O_2$ sensor with a relatively long lifetime. The diagrams help to define and provide the basis for a theoretical calculation of the thermodynamic voltage window (TVW) and as an indication of the experimental voltage window of the sensor (EVW), which may assure stable sensor operation in the presence of electrochemical modifications of electrolytes and electrodes.

In general, the Thermodynamic Voltage Window (TVW) is defined herein as the voltage gap between the equilibrium electrode potential of the anode and the oxygen potential in the same electrolyte. This can be calculated from the appropriate Pourbaix diagrams in the alkali electrolyte (at the same pH). The TVW values are provided above for Cu, Bi, Pb and Sb, where Sb has the highest value of 1.076 V. Similarly, the Experimental Voltage Window (EVW) is obtained from biasing the $O_2$ sensor and measuring the sensor current. A high value of the EVW may be used to guarantee reliable sensor operation in the limiting current region determined by the geometrical sensor design.

It is expected that for a larger TVW, the EVW would also be larger. From this point of view (and ignoring the operating environment), Sb could be a better anode with respect to Cu or even Bi.

In this regard, antimony (Sb) will be considered first. Antimony is a fairly noble metal (thermodynamically stable in water) in the whole pH range of from −2 to +16. An alkaline or acid electrolyte can be used as the electrolyte 18 in the sensor 10. It can be seen that there is no self-corrosion due to H2 evolution at the anode or self corrosion due to $H_2$ evolution at the cathode.

The process of oxygen sensing (detection) may be characterized as follows.

Cathode:

Carbon platinized with 5% platinum is used for $O_2$ reduction reaction

$$O_2+2H_2O+4e^-=4OH^- \qquad \text{equation [1]}$$

Anode:

Pure antimony for antimony oxidation reaction with 3 electron production per each Sb atom

$$2Sb+3H_2O=Sb_2O_3+6H^++6e^- \qquad \text{equation [2]}$$

Cell Reaction:

$$2Sb+3O_2=2Sb_2O_3 \qquad \text{equation [3]}$$

Electrolyte:

An alkaline electrolyte like potassium acetate ($CH_3COOK$) (KOAc), KOH or organic bases (like ammonium quaternary hydroxide ($R4N^+OH^-$) with pH in the range from 7 to 14 could be used for the Sb-based galvanic cell. The oxidation reaction products are soluble in the electrolyte. As such, a fast response time of the sensor may be obtained.

In the case of alkali electrolyte, according to the equilibrium reactions theory, a 3-electron $Sb/Sb_2O_3$ reaction (equation [3]) may take place, while the electrode potential of the anode will lay at 0.1 V vs NHE, which is a more cathodic potential with respect the Pb (0.25 V vs NHE), Cu (0.47 V vs NHE) or Bi (0.37 V vs NHE) potentials when immersed in the same electrolyte (see FIG. 1 of the publication Atlas of Electrochemical Equilibria in Aqueous Solutions, 1974, page 527). All the above potential values are estimated with respect to the Normal Hydrogen Electrode (NHE), by using Pourbaix diagrams of those chemical elements A coulombic characterization of the Sb-alkaline electrolyte oxygen galvanic sensor 10 for the case of a sensor current of 100 microamperes and with an operation time of two years may be illustrated as follows. In this regard, the Standard Antimony atomic weight of antimony, Aw=121.76 g/mol. The Faraday constant, F=96485 Coulomb/mole. The number of electron release by dissolution of one atom of antimony, n=3, according to the theoretical predictions.

In this case, the equivalent weight, Aw/n=40.58 and the capacity (A hr/g)=n*F/(Aw*3600)=0.66 (This is higher than in the case of Cu in the same electrolyte (0.42)). The sensor current, I=100 µA in the case of continuous sensor operation for 2 years. Using this information, the minimum weight of an anode 16 may be calculated. In this regard, the antimony anode weight=31.536 Aw I t/nF=2.6 grams (t is given in years and I is given in microamperes). Similarly, the Sb mass for 2-years operation in alkali is much less than the 4.2 grams needed for Cu in the same electrolyte.

The electrolyte design considerations for the above $O_2$ galvanic sensor based on Sb-alkali electrolyte will be discussed next. In this regard, the envisioned alkali electrolytes for cell operation are: KOAc or inorganic bases like KOH or NaOH or organic bases such as ammonium quaternary hydroxide, $R_4N^+OH^-$. As shown in the overall cell reaction (equation [3]), the electrolyte will not be consumed by the sensing reaction.

It may be noted that water is not involved in the overall electrochemical cell reaction, therefore the water balance will be governed by external RH and temperature as in comparable lead sensors. Even if the alkaline electrolytes show some hygroscopic properties, they will not be as efficient as strong acids (like $H_2SO_4$) for water management in dry ambient conditions.

Anode reaction products may be considered next. In the case of antimony anodes, according to Pourbaix theory, in the absence of oxidizing agents in the electrolyte, there is no passivation region in the entire pH-voltage range of conditions (FIG. 2, page 528 of Atlas of Electrochemical Equilibria in Aqueous Solutions). However, in practice, aerated water can attack antimony converting it into fairly soluble antimonious anhydride, $Sb_2O_3$. $Sb_2O_3$ could be thermodynamically stable in the presence of water free from reducing agents and strong oxidizing agents. More alkaline electrolyte solutions dissolve the oxide (pH>13) as antimonite ions $SbO_2^-$. In the design of the sensor, an electrolyte chamber with empty space may be needed in order to accommodate the possible insoluble and/or soluble product.

The use of bismuth for the anode 16 of the sensor 10 will be considered next. In this regard, bismuth is a fairly noble metal (it is thermodynamically stable in water). The $Bi/Bi_2O_3$ couple has a potential of about 0.37 V versus the Normal Hydrogen Electrode (NHE). There is no self-corrosion due to $H_2$ evolution at the anode and no self corrosion due to $H_2$ evolution at the cathode. Bismuth has an energy density of 0.38 (A*h/gram). The potential difference between anode and cathode may be higher than that of a Cu anode. Finally, bismuth is commercially available and is not toxic.

When used as an anode 16 in the sensor 10, the electrochemical process may be described as follows.

Cathode:
Carbon platinized with 5% platinum is used for $O_2$ reduction $$3O_2+6H_2O+12e^-=12OH^- \qquad \text{equation [4]}$$

Anode:
Pure bismuth with a large area with respect to the cathode $$4Bi+6H_2O=2Bi_2O_3+12H^++12e^- \qquad \text{equation [5]}$$

Cell Reaction:

$$4Bi+3O_2=2Bi_2O_3 \qquad \text{equation [6]}$$

Electrolyte:
A neutral and alkali aqueous solution may be used, including potassium acetate (KOAc), potassium hydroxide (KOH), sodium hydroxide (NaOH) or organic bases like ammonium quaternary hydroxide ($R_4N^+OH^-$), where R could be: methyl, ethyl, propyl, butyl, or a combination of these.

According to the theoretical predictions, in the case of bismuth immersed in an alkali electrolyte, the 3-electron $Bi/Bi_2O_3$ anode reaction (equation [5]) may take place with an electrode potential of 0.37 V with respect to NHE which is less than the potential of copper/$Cu_2O$, Cu (0.47 V vs NHE) when immersed in the same electrolyte (see FIG. 1 of the publication Atlas of Electrochemical Equilibria in Aqueous Solutions, 1974, page 536). All the above potential values are estimated with respect to the Normal Hydrogen Electrode (NHE), by using Pourbaix diagrams of those chemical elements.

A coulombic characterization of the Bi-alkaline electrolyte oxygen galvanic sensor for the case of a sensor current of 100 microamperes and with an operation time of two years may be performed. In this regard, the standard Bismuth atomic weight, Aw=210 g/mol, the faraday constant, F=96485 Coulomb/mole, the number of electron release by dissolution of one atom of bismuth, n=3, the equivalent weight, Aw/n=70, the capacity (A hr/g)=n*F/(Aw*3600) =0.38, the sensor current, I=100 μA and continuous sensor operation is assumed for 2 years. In this case, the bismuth anode weight=31.536 Aw I t/nF=4.58 grams (t is given in years and I is given in microamperes).

Electrolyte design considerations for the $O_2$ galvanic sensor based on Bi-alkali electrolyte will be discussed next. In this regard, the envisioned alkali electrolytes for cell operation are: KOAc (for a drop-in replacement) or inorganic bases like KOH or NaOH or organic bases such as an ammonium quaternary hydroxide, $R_4N^+OH^-$. As shown in the overall cell reaction (equation [6]), the electrolyte will not be consumed by the sensing reaction.

As above, water is not involved in the overall electrochemical cell reaction, therefore the water balance will be governed by external RH and temperature as in the lead reference example. As shown above, the alkaline electrolyte will be less efficient in water management in dry ambient conditions, with respect to strong acids based electrolytes.

Anode reaction products may be considered next. In neutral and alkaline electrolyte, the bismuth oxidation will form $Bi_2O_3$, a stable product in the presence of water (even aerated water) and most neutral and alkaline aqueous solutions. Empty space in the electrolyte chamber may need to be provided in order to accommodate the soluble product.

Copper (Cu) for the anode 16 will be considered next. In this regard, copper is thermodynamically stable in water, does not oxidize or form complex agents in the whole pH range from −2 to +15. There is no self-corrosion due to $H_2$ evolution at the anode and no self corrosion due to H2 evolution at the cathode.

A strong $H_3PO_4$ acid can be used as the electrolyte 18 in the sensor 10 using a copper anode 16. $CO_2$ rejection is provided by the strong $H_3PO_4$. $H_3PO_4$ is hygroscopic and reduces the effects of drying out.

Copper has a high energy density (capacity of 0.84 Ahr/g). In addition, copper is commercially available and can be easily manufactured in the form of wires.

The process of oxygen detection in the sensor 10 using a copper anode 16 may be characterized as follows.

Cathode:
Carbon platinized with 5% platinum is used for $O_2$ reduction $$O_2+4H^++4e^-=2H_2O \ (1.23 \text{ V vs SHE}) \qquad \text{equation [7]}$$

Anode:
Pure copper with a large surface area (wool, wire) is used for a copper oxidation reaction that forms cupric ions $$2Cu=2Cu^{++}+4e^- (Eo=0.520+0.0591 \log(Cu^{++}) \text{ vs SHE} \qquad \text{equation [8]}$$

Cell Reaction:

$$2Cu+O_2+4H^+=2Cu^{++}+2H_2O \qquad \text{equation [9]}$$

From the above reactions, it can be seen that in acid electrolytes, four hydrogen ions (protons) are consumed for each four electrons consumed by the (cathodic) reduction reaction, as a result of each two copper atoms being dissolved to cupric ions. Therefore, the acid electrolyte is depleted of protons during cell operation, and therefore its pH value is increasing. However, by electrolyte design, as per FIG. 7, the pH should remain below 2.5, to preserve the $O_2$ sensor operation as per the above cell reaction.

The electrolyte 18 in a sensor 10 using a copper anode 16 may be an aqueous solution of strong phosphoric acid, or methane sulfonic acid (MSA). Both are able to provide enough protons. Citric acid may be added to electrolyte to delay formation of copper phosphates/methane sulfonates. In the case of an acid electrolyte, with a pH lower than 2.5 (see FIG. 7), the 2-electron $Cu/Cu^{++}$ reaction may take place (equation [8]), while the electrode potential of the anode remains at a much greater cathodic potential than when the copper anode is immersed in the alkaline electrolyte (see FIG. 1, as per the publication Atlas of Electrochemical Equilibria in Aqueous Solutions, 1974, page 387).

A coulombic characterization of the Cu-strong acid based oxygen galvanic sensor 10 for the case of sensor current of 100 microamperes and with an operation time of two years may be performed as follows. A calculation of minimum copper anode mass may be performed first. In this regard, copper has an atomic mass, Aw=64 and a Faraday constant, F=96494 Coulomb/mole. The number of electrons released by dissolution of one atom of copper, n=2 and the equivalent weight=Aw/n=32. The capacity (A hr/g)=n*F/(Aw*3600) =0.84 (Equation A).

It may be assumed that the sensor current (I=100 µA) and the sensor 10 is in continuous operation of 2 years. Under these conditions the copper anode weight=31.536 Aw I t/nF=2.1 g (t is given in years and I is given in microamperes) (Equation B).

Electrolyte design considerations for the $O_2$ galvanic sensor 10 based on copper in a strong acid will be discussed next. In this regard, the criteria for electrolyte selection in the case of a copper anode may include the following aspects: strong acidity, forms highly solubility salts, has a low (acceptable) corrosion rate of the copper, has low toxicity, has chemical stability and has enhanced dissolution and removal of salts. The envisioned strong acid electrolytes for cell operation are: phosphoric acid ($H_3PO_4$) and methane sulphonic acid (MSA) $CH_3SO_3H$.

Phosphoric acid is a triprotic molecule and can dissociate up to three times as shown below:

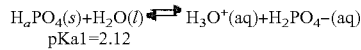
pKa1=2.12

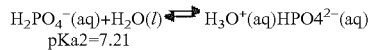
pKa2=7.21

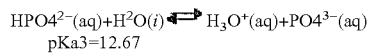
pKa3=12.67

From the pka values shown, one can see that in order to maintain the pH lower than 2.5 only the first proton can be taken into account.

From the above pKa values, one can deduce that $H_3PO_4$ is a weak triprotic acid, and, only the first proton is easily released in the electrolyte. The successive reactions of releasing the second and the third proton from the $H_3PO_4$ molecule are much less energetically favored. From the above data, it has been found that it is necessary to have a reservoir of protons in the electrolyte sufficient so that (at the end of the sensor life), when the entire copper mass of 2.1 gram is consumed, there are enough hydrogen ions to provide a pH smaller than 2.5:

An example of the calculations of the electrolyte volume needed for copper-strong acid electrolyte cell 10 is as follows. In this regard, the copper mass of the anode 16, m=2.1 gram, l=100 µA and t=2 years. The electrolyte 18 is an 65% aqueous solution of $H_3PO_4$ with molarity of 11.62 M (i.e. 11.62 g of Fr/liter of solution). The mass of protons consumed=1×32.536*l*t/F=0.0654 grams of $H^+$ (as per equation B). Simple calculations show that such an amount of protons is hosted in a volume of 9 ml of a 65% $H_3PO_4$ acid electrolyte. Therefore, if an 18-20 ml of $H_3PO_4$ 65% aqueous solution were chosen as an electrolyte, this would provide a sufficient proton reservoir, and prevent H+ depletion in the electrolyte at the end of the copper consumption. These coulombic calculations show that this sensor which is based on copper anode and acid electrolytes may have bigger sizes with respect to present lead-based galvanic $O_2$ sensors, if no other design changes are performed in the lead-replacement process.

The electrochemical properties of the Methane Sulphonic Acid may be considered next. In this regard, Methane sulfonic acid (MSA) has the chemical formula $CH_3SO_3H$ and includes all the above mentioned properties. MSA is a strong organic acid (pKa=−1.92) which dissociates almost completely in water according to the reaction:

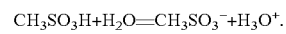

Anode reaction products may be considered next. In this regard, the cupric ions resulting from the copper dissolution in the acid electrolyte will further interact with the acid electrolyte. A soluble salt of $Cu(H_2PO4)_2$ may be obtained from the interaction of cupric ions and phosphate anions ($H_2PO4^-$). In such an advantageous situation, the copper anode surface may be preserved clean, free of any passivation layer, and this may maintain a good response time of the sensor as well as a good lifetime. However, the formation of the soluble salts of copper phosphate may deplete the electrolyte of phosphate anions decreasing the ionic strength of the electrolyte. In the same time period, due to phosphate anions consumption, the water will tend to go out of the cell which will increase again the solution molarity with the formation of empty space in the cell. By using a sufficiently large reservoir of electrolyte of about 20 ml, there will be plenty of $H_2PO_4^-$ to support the necessary ionic strength. However, if it is necessary to delay the process of copper phosphate formation, other steps may be taken. Here the addition of an organic acid like citric to $H_3PO_4$, which may be beneficial in boosting $Cu^{++}$ solubility by forming a complex solution, thereby delaying the onset of phosphate ion depletion by precipitation of copper phosphate.

An alkaline electrolyte 18 for use with a copper anode 16 may be considered next. The process of oxygen detection by the sensor 10 may be characterized as follows.

Cathode:
Carbon platinized with 5% platinum is used for $O_2$ reduction

 equation [10]

Anode:
Pure copper with large surface area (wool, wire) is used for copper oxidation reaction

 equation [11]

Cell Reaction:

 equation [12]

The alkaline electrolyte 18 may include KOH, NaOH or an organic base with a pH in the range from 7 to 14 in the case of the copper based galvanic cell 10. In the case of alkali electrolyte, a one electron $Cu/Cu_2O$ reaction (equation [11]) is taking place, while the electrode potential of the anode will operate at a greater anodic potential than with respect to the situation when the copper anode is immersed in the acid electrolyte (see FIG. 3 of the publication Atlas of Electrochemical Equilibria in Aqueous Solutions, 1974, page 387).

A coulombic characterization of the Cu-alkaline electrolyte oxygen galvanic sensor 10 for the case of sensor current of 100 microamperes and with an operation time of two years may be performed for this situation as follows. In this situation, the atomic mass of copper, Aw=64 and the Faraday constant, F=96494 Coulomb/mole. The number of electrons released by dissolution of one atom of copper, n=1. Copper has an equivalent weight=Aw/n=6. The capacity (A hr/g) =n*F/(Aw*3600)=0.42, the sensor is assumed to have a current=I=100 µA and continuous sensor operation of 2 years is assumed. In this situation, the copper anode weight=31.536 Aw I t/nF=4.2 g (t is given in years and I is given in microamperes).

A simple comparative analysis of the electrochemical properties of two copper-electrolyte systems shows that the copper-acid electrolyte system performs better, as it has higher energy storage capacity and requires less copper mass for the same lifetime of the copper-alkaline sensor operating at the same sensor current, but it requires a much higher volume of electrolyte, in order to avoid proton depletion during long term sensor operation. In addition, a larger potential difference for the cell can be obtained.

The electrolyte design considerations for the $O_2$ galvanic sensor based on copper-alkali electrolyte is discussed next. In this regard, the envisioned alkali electrolytes for cell operation are: inorganic bases like KOH or NaOH or organic bases such as ammonium quaternary hydroxide, $R_4N^+OH^-$. As shown in the overall cell reaction (equation [12]), the electrolyte will not be consumed in the sensing reaction.

It should be noted that as above, water is not involved in the overall electrochemical cell reaction and therefore the water balance will be governed by external RH and temperature as in the lead reference example. The alkaline electrolyte is less hygroscopic that the strong acids, and therefore it will not be as effective for water management in dry ambient conditions, as it is a strong acid.

Anode reaction products may also be considered. In neutral and alkaline electrolyte, the copper oxidation will form cuprous oxide as an insoluble product. Enough empty space in the electrolyte chamber may need to be provided in order to accommodate the insoluble product.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A lead-free, self-corrosion-free electrochemical galvanic oxygen sensor comprising:
    a container, the container further comprising:
        a lead-free anode,
        an electrolyte, wherein the electrolyte is an organic base of an alkaline aqueous solution of ammonium quaternary hydroxide, $R_4N^+OH$;
        a cathode, and
        a current collector,
        wherein the container further includes a diffusion barrier that causes the sensor to operate in a limiting current region.

2. The sensor of claim 1, where the anode is selected from metals and metalloids which have a thermodynamic immunity region in common with a water stability domain in a pH range from 7 to 16.

3. The sensor of claim 2, where a voltage difference between an equilibrium potential of the couple Me/metal oxide and an equilibrium potential of a normal hydrogen electrode in the same electrolyte is in a range of (0.15-0.37 V).

4. The sensor of claim 3, where the anode contains bismuth, antimony or copper.

5. The sensor of claim 4, where the anode is shaped as an array of wires, a disc, or granules, powders, or pellets.

6. The sensor of claim 1, where R further comprises methyl, ethyl, propyl, butyl, or a combination of two or more of methyl, ethyl, propyl and butyl.

7. The sensor of claim 6, where the electrolyte is any combination of the above organic alkali electrolytes.

8. The sensor of claim 1, where the cathode includes carbon platinized with 5% platinum, or gold, or silver.

9. An electrochemical galvanic oxygen sensor comprising:
    a copper anode;
    an electrolyte, wherein the electrolyte is an organic base of an alkaline aqueous solution of ammonium quaternary hydroxide, $R_4N^+OH$;
    a carbon/platinum cathode;
    a nickel wire current collector; and
    a diffusion barrier configured to cause the electrochemical galvanic oxygen sensor to operate in a current limiting region.

* * * * *